US00PP32548P2

(12) United States Plant Patent
Wood

(10) Patent No.: US PP32,548 P2
(45) Date of Patent: Dec. 1, 2020

(54) ***HYDRANGEA* PLANT NAMED 'SMNHSI'**

(50) Latin Name: *Hydrangea serrata*
Varietal Denomination: SMNHSI

(71) Applicant: Spring Meadow Nursery, Inc., Grand Haven, MI (US)

(72) Inventor: Timothy D Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 16/602,614

(22) Filed: Nov. 7, 2019

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02; A01H 5/00
See application file for complete search history.

*Primary Examiner* — Kent L Bell
(74) *Attorney, Agent, or Firm* — Cassandra Bright

(57) ABSTRACT

A new and distinct cultivar of *Hydrangea* plant named 'SMNHSI' is disclosed, characterized by floriferous plants producing mophead and lacecap inflorescences with double whorled flowers. Plants are strong rebloomers, and cold hardy to USDA Zone 4. The new variety is a *Hydrangea*, normally produced as an ornamental plant.

4 Drawing Sheets

Latin name of the genus and species: *Hydrangea serrata.* Variety denomination: 'SMNHSI'.

BACKGROUND OF THE INVENTION

The new *Hydrangea* cultivar is a product of a planned breeding program conducted by the inventor, at a commercial nursery in Grand Haven, Mich. The objective of the breeding program was to produce new *Hydrangea* varieties with new forms, colors, and better habits. The open pollination resulting in this new variety was made during Summer of 2012.

The seed parent is the variety *Hydrangea serrata* 'MAK20', U.S. Plant Pat. No. 24,820. The pollen parent is unknown, as this was the result of open pollination. The new variety was identified as a potentially interesting selection in the Summer of 2014 at a commercial greenhouse in Grand Haven, Mich. Date of first sale was Jun. 25, 2019, occurring in the United States. This sale was made directly by the inventor or one who obtained the claimed invention directly or indirectly from the inventor. This sale and all public disclosures made between Jun. 25, 2019 and the filing of this application fall within the exception allowed under 102(b)(1).

Asexual reproduction of the new cultivar 'SMNHSI' by vegetative softwood cuttings was first performed during the Summer of 2014, at a commercial greenhouse in Grand Haven, Mich. Subsequent asexual propagation has shown that the unique features of this cultivar are stable and reproduced true to type in 5 successive generations.

SUMMARY OF THE INVENTION

The cultivar 'SMNHSI' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNHSI' These characteristics in combination distinguish 'SMNHSI' as a new and distinct *Hydrangea* cultivar:

1. Strong reblooming.
2. Double whorled flowers.
3. Good cold hardiness, to USDA Zone 4.
4. Both lacecap and mophead inflorescences present on plants.

PARENT COMPARISON

Plants of the new cultivar 'SMNHSI' are similar to plants of the seed parent in most horticultural characteristics, however, plants of the new cultivar 'SMNHSI' differ in the following;

1. The new variety has double whorled flowers, while the seed parent has single flowers.
2. The new variety produces lacecap and mophead inflorescences, while the seed parent produces lacecap.

COMMERCIAL COMPARISON

Plants of the new cultivar 'SMNHSI' can be compared to the variety *Hydrangea serrata* 'SMNHSDD', U.S. Plant Pat. No. 29,832. These varieties are similar in most horticultural characteristics; however 'SMNHSI' differs in the following:

1. The new variety has lacecap and mophead inflorescences, while this comparator is lacecap.
2. The new variety is more floriferous than this comparator.
3. The new variety has narrower leaves than this comparator.

BRIEF DESCRIPTION OF THE PHOTOGRAPHS

'SMNHSI' is illustrated by the accompanying photographs which show the plant's form, foliage, and inflorescences. The colors shown are as true as can be reasonably obtained by conventional photographic procedures. Colors in the photographs may differ slightly from the color values cited in the detailed botanical description, which accurately describe the colors of the new hybrid *Hydrangea*. Age of the plants photographed is between 2 to 3 years.

DETAILED BOTANICAL DESCRIPTION

Figure 1:
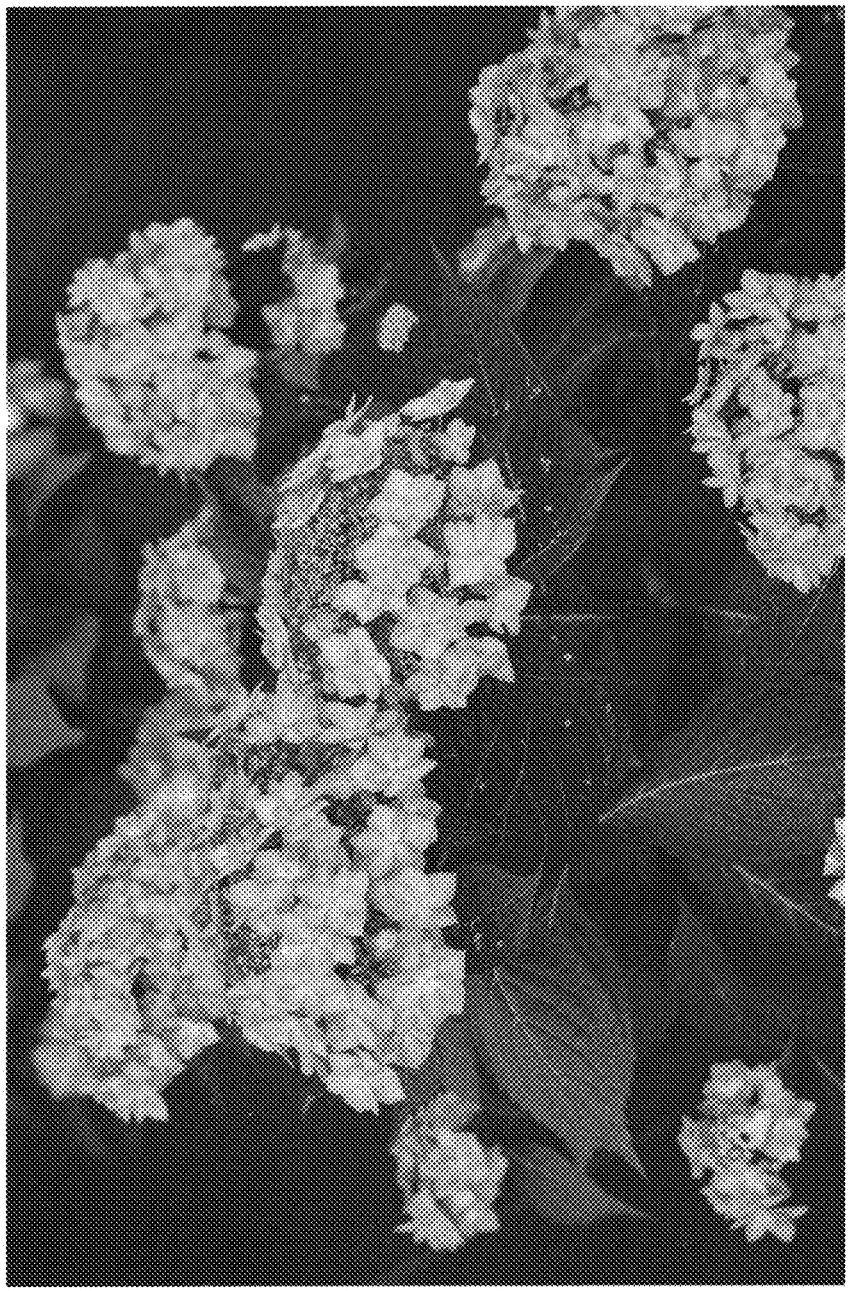
FIG. 1 shows the developing inflorescence of a container-grown plant, treated with a typical acidic "bluing"(aluminum sulfate) treatment, grown in a greenhouse in Grand Haven, Mich. in 2019.
Figure 2:
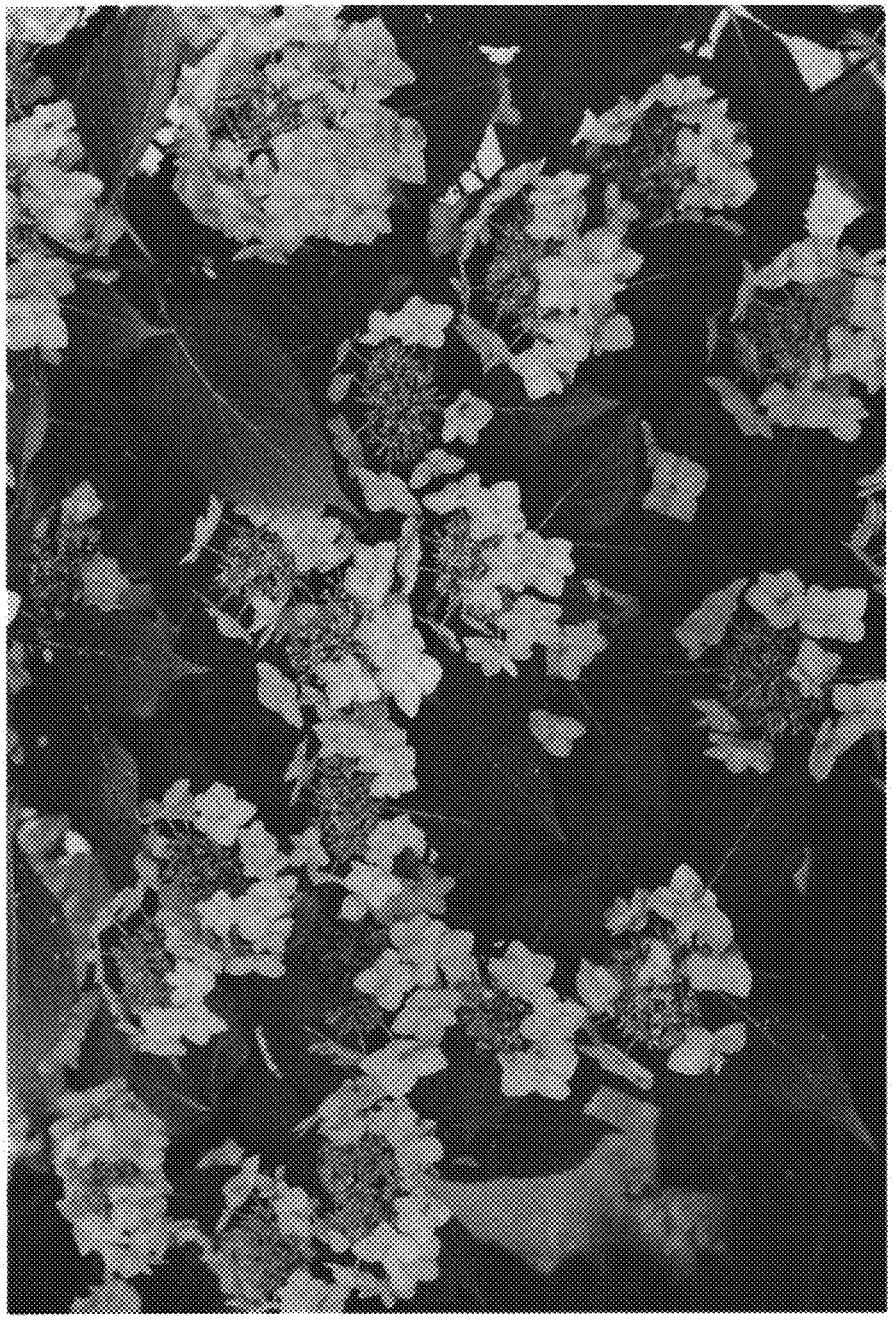
FIG. 2 shows the developing inflorescence of a container-grown plant, treated without "bluing" treatment, grown in a greenhouse in Grand Haven, Mich. in 2019.
Figure 3:
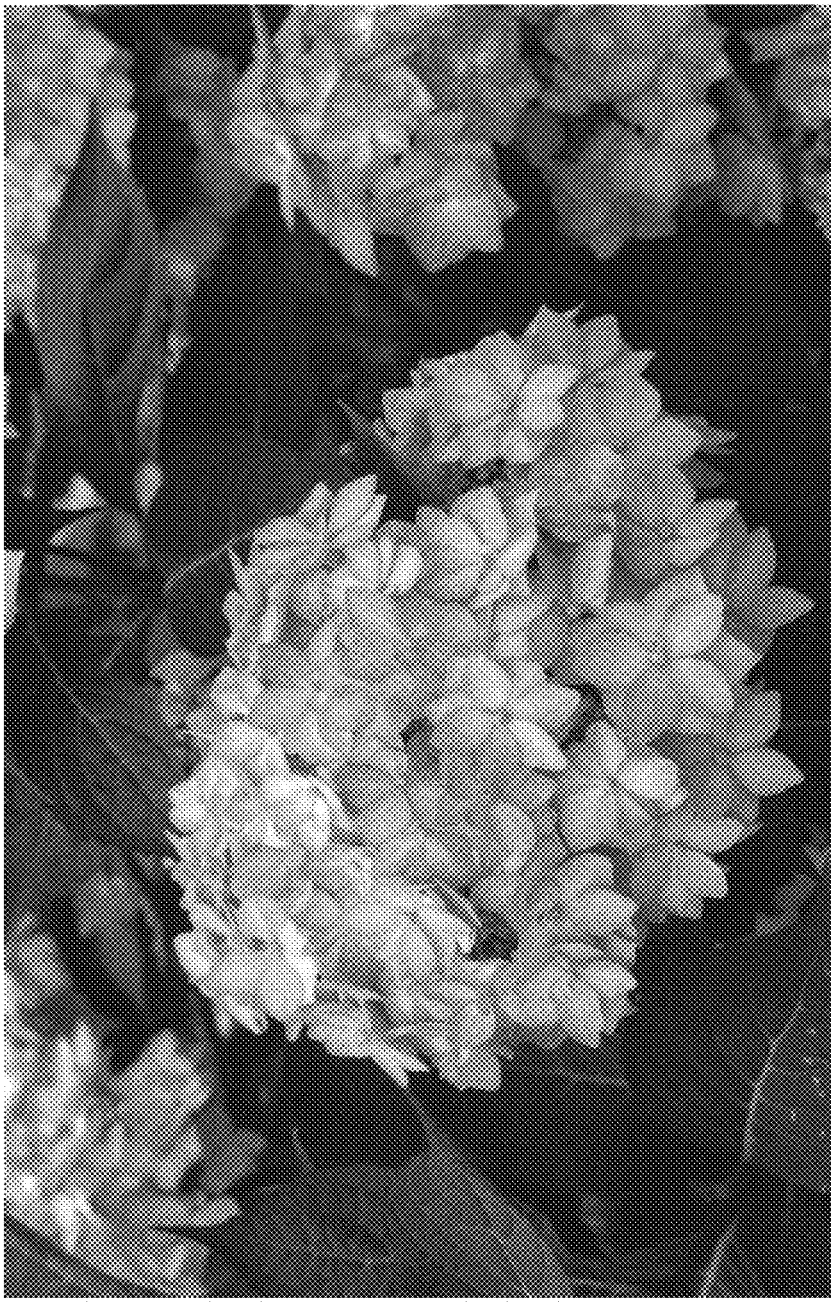
FIG. 3 shows the mature inflorescence of a container-grown plant, treated without "bluing" treatment, grown in a greenhouse in Grand Haven, Mich. in 2019.
Figure 4:
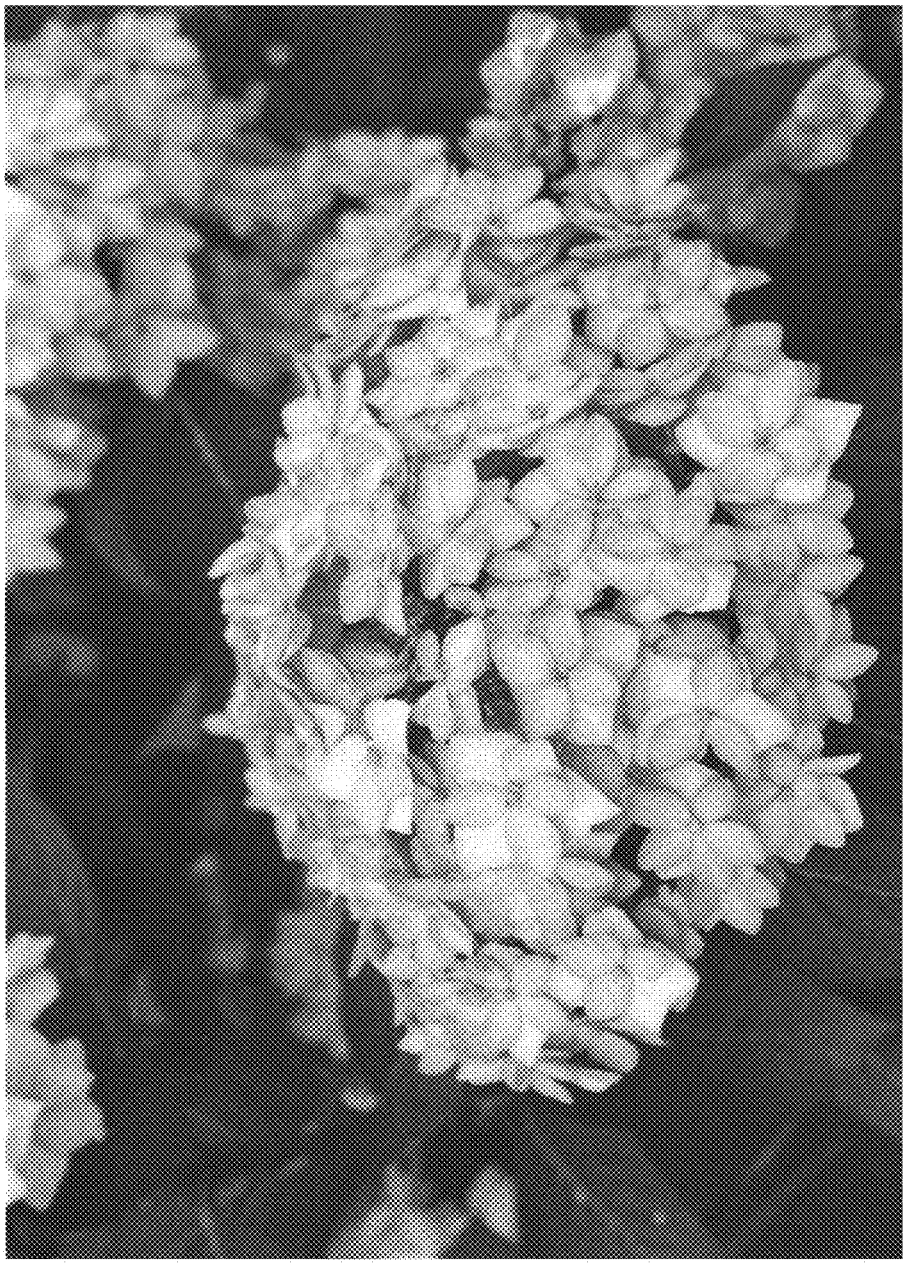
FIG. 4 shows the mature inflorescence of a container-grown plant, treated with a typical acidic "bluing"(aluminum sulfate) treatment, grown in a greenhouse in Grand Haven, Mich. in 2019.

In the following description, color references are made to The Royal Horticultural Society Colour Chart 2015 except where general terms of ordinary dictionary significance are used. The following observations and measurements describe 'SMNHSI' plants grown in a commercial poly greenhouse in Grand Haven, Mich. under natural lighting. Measurements were taken during Summer of 2019. The plants were about 4 years old planted in the ground. The growing temperature ranged from 5° C. to 27° C. Measurements and numerical values represent averages of typical plant types.

Botanical classification: *Hydrangea serrata* 'SMNHSI'.

PROPAGATION

Time to initiate roots: Approximately 18 days.

Time to produce a rooted young plant: Approximately 30 days.

Propagation method: Softwood cuttings.

PLANT

Plant type: Flowering deciduous perennial shrub.

Age of plant described: Approximately 2 to 3 years old.

Growth habit: Upright and outward.

Overall plant shape: Upright.

Height: 50 cm.

Plant spread: 78 cm.

Growth rate: Moderate.

Plant vigor: Good.

Branching habit: Basal.

Length of primary lateral branches: 46 cm.

Diameter of lateral branches: 5 mm.

Quantity of lateral branches: 20 to 30.

Stem:

- *Stem shape*.—Round.
- *Stem strength*.—Good.
- *Color*.—Immature: RHS Yellow-Green 144B. Mature: RHS Yellow-Green 144B.
- *Pubescence*.—Yes, near inflorescence.
- *Aspect*.—5 to 60°.
- *Lenticels*.—Along stem, colored RHS Greyed-Purple N187B.

Internode length: 8.5 cm.

Root description: Moderately dense, thick main roots with fine, fibrous secondary roots. Main roots colored near Brown 200D, secondary roots near Yellow-White 158D.

FOLIAGE

Leaf:

- *Arrangement*.—Opposite.
- *Leaf shape*.—Elliptic to obovate.
- *Average length*.—14 cm.
- *Average width*.—7 cm.
- *Apex*.—Acuminate.
- *Base*.—Obtuse.
- *Margin*.—Serrate.
- *Texture of top surface*.—Smooth, rugose, leathery.
- *Texture of bottom surface*.—Smooth, leathery, prominent veins.
- *Leaf pubescence*.—On veins, under side.
- *Color*.—Young foliage upper side: RHS Green 139A. Young foliage under side: RHS Green NN137C. Mature foliage upper side: RHS Grey Green N189A. Mature foliage under side: RHS Green NN137C.
- *Venation*.—Pattern: Pinnate-arculate. Color upper side: RHS Yellow-Green N144B. Color under side: RHS Yellow-Green 145C.
- *Petiole*.—Average Length: 1 cm. Diameter: 5 mm. Petiole color upper side: RHS Yellow Green N144B to Greyed-Orange 176A. Petiole color lower side: RHS Yellow Green N144B to Greyed-Orange 176A. Petiole Texture upper side: Smooth. Petiole Texture lower side: Smooth.

FLOWER

Natural flowering season: May to July.

Inflorescence:

- *Type*.—Semi-mophead.
- *Quantity of flowers per inflorescence*.—Fertile flowers: 20-200 depending on shape of inflorescence. Sterile flowers: 70 to 220.
- *Persistent or self-cleaning*.—Persistent, self-cleaning after several weeks.
- *Longevity*.—Individual flowers stay fresh on the plant for about 2 weeks. Inflorescences are ornamental for several weeks.
- *Fragrance*.—None detected.

Panicle:

- *Shape*.—Umbel.
- *Height*.—7 cm.
- *Diameter*.—14 cm.

Sterile flower:

- *Bud shape*.—Spherical.
- *Bud length*.—3 mm.
- *Bud diameter*.—4 mm.
- *Bud color*.—Acidic: RHS Purple 77B to Violet-Blue 97A. Basic: RHS Red-Purple 68D.
- *Flower aspect*.—Upright.
- *Flower shape*.—Obovate.
- *Flower length*.—1 cm.
- *Flower diameter*.—1 cm.
- *Persistence*.—Persistent.

Sterile flower petals:

- *Petal arrangement*.—Whorl, overlapping.
- *Quantity*.—9.
- *Length of petal*.—4 mm.

*Width of petal.*—2 mm.
*Apex.*—Acute.
*Shape of petal.*—Ovate.
*Petal margin.*—Entire.
*Petal base.*—Truncate.
*Petal texture.*—Smooth, upper and under side.
*Color.*—Upper surface at first opening: Acid: RHS Violet-Blue 94C. Basic: RHS Red-Purple 73C. Under surface at first opening: Acid: RHS Violet-Blue 94C. Basic: RHS Red-Purple 73C. Upper surface at maturity: Acid: RHS Violet-Blue 94C. Basic: RHS Red-Purple 73C. Under surface at maturity: Acid: RHS Violet-Blue 94C. Basic: RHS Red-Purple 73C.

Sterile flower sepal:
*Arrangement.*—Double whorl.
*Number.*—9 or 10.
*Shape.*—Irregular and elliptic to deltoid.
*Tip.*—Acute.
*Base.*—Acute to obtuse.
*Margin.*—Crenate.
*Length.*—Average 2.5 to 4 cm.
*Width.*—Average 2 to 3 cm.
*Texture, upper.*—Smooth.
*Texture, lower.*—Smooth.
*Color.*—Upper surface at first opening: RHS Yellow Green 145C. Under surface at first opening: RHS Yellow Green 145C. Upper surface at maturity: Acidic: RHS Violet-Blue 94B in the center to Purple 77C towards the top and margins. Basic: RHS Red-Purple 73A to 69D. Under surface at maturity: Acidic: RHS Violet Blue 91C to 91D to Red-Purple 67D. Basic: RHS Red-Purple 73D.

Sterile flower pedicel:
*Length.*—2.5 cm.
*Diameter.*—1 mm.
*Angle.*—45-90° from vertical.
*Strength.*—Good.
*Texture.*—Slightly pubescent.
*Color.*—Acidic: RHS Violet 85C. Basic: RHS Red-Purple 70D.

Fertile flower:
*Bud shape.*—Orbicular.
*Bud length.*—4 mm.
*Bud diameter.*—4 mm.
*Bud color.*—Acidic: RHS Purple 75A. Basic: RHS Purple 75B.
*Flower aspect.*—Upright and outward.
*Flower shape.*—Double whorl.
*Flower diameter.*—13 mm.
*Flower length.*—13 mm.
*Flower depth.*—2 mm.
*Longevity.*—1 to 2 weeks.
*Persistence.*—Self-cleaning.

Fertile flower petals:
*Arrangement.*—Double whorl.
*Quantity.*—14.
*Length of petal.*—4 mm.
*Width of petal.*—2 mm.
*Apex.*—Acute.
*Shape of petal.*—Concave-elliptic.
*Petal margin.*—Entire.
*Petal base.*—Acute-truncate.
*Petal texture.*—Smooth, upper and under side.
*Color.*—Upper surface at first opening: Acidic: RHS Violet Blue 94C. Basic: RHS Red-Purple 73C. Under surface at first opening: Acidic: RHS Violet Blue 94C. Basic: RHS Red-Purple 73C. Upper surface at maturity: Acidic: RHS Violet Blue 94C. Basic: RHS Red-Purple 73C. Under surface at maturity: Acidic: RHS Violet Blue 94C. Basic: RHS Red-Purple 73C.

Fertile flower sepal:
*Arrangement.*—Whorled.
*Number.*—6.
*Shape.*—Lanceolate.
*Tip.*—Obtuse.
*Base.*—Truncate.
*Margin.*—Entire.
*Length.*—1 mm.
*Width.*—1 mm.
*Texture, upper.*—Smooth.
*Texture, lower.*—Smooth.
*Color.*—Upper surface at first opening: RHS Yellow Green 145B. Under surface at first opening: RHS Yellow Green 145B. Upper surface at maturity: RHS Yellow Green 145B. Under surface at maturity: RHS Yellow Green 145B.

Fertile flower pedicel:
*Angle.*—0-45°.
*Strength.*—Strong.
*Length.*—5 mm.
*Width.*—1 mm.
*Texture.*—Smooth.
*Color.*—RHS Yellow Green 145B.

REPRODUCTIVE ORGANS

Sterile flowers:
Stamens:
*Number.*—10.
*Filament length.*—8 mm.
*Filament color.*—RHS Violet-Blue 94C.

Anthers:
*Shape.*—Bi-lobed.
*Length.*—9 mm.
*Color.*—RHS Violet-Blue 94C.
*Pollen color.*—RHS Greyed-Yellow 160B.
*Pollen amount.*—Moderate.

Pistil:
*Number.*—6.
*Length.*—3 mm.
*Stigma.*—Shape: Globose. Color: RHS Violet-Blue 94C.

Fertile flowers:
Stamens:
*Number.*—Average 15.
*Filament length.*—4 mm.
*Filament color.*—RHS Violet-Blue 94C.

Anthers:

*Shape*.—Bi-lobed.

*Length*.—1 mm.

*Color*.—RHS Violet-Blue 94C.

*Pollen color*.—RHS Greyed-Yellow 160B.

*Pollen amount*.—Moderate.

Pistil:

*Number*.—5 to 7.

*Length*.—3 mm.

*Style*.—Length: 3 mm. Color: RHS Violet-Blue 94C.

*Stigma*.—Shape: Globose. Color: RHS Violet-Blue 94C.

OTHER CHARACTERISTICS

Seeds and fruits: None observed.

Disease/pest resistance: Neither resistance nor susceptibility to normal diseases and pests of *Hydrangea* have been observed.

Temperature tolerance: USDA Zones 4 to 9.

What is claimed is:

1. A new and distinct cultivar of *Hydrangea* plant named 'SMNHSI' as herein illustrated and described.

* * * * *